(12) United States Patent
Kost et al.

(10) Patent No.: US 8,343,134 B2
(45) Date of Patent: Jan. 1, 2013

(54) SYSTEM AND METHOD FOR TRANSFETAL (AMNION-CHORION) MEMBRANES TRANSPORT

(75) Inventors: Joseph Kost, Omer (IL); Israel Patla, Beer-Sheva (IL); Avraham Schroeder, D.N. Sde Gat (IL); Lior Wolloch, Kiriat Mozkin (IL); Mordechi Hallak, Ra'anana (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 751 days.

(21) Appl. No.: 12/308,244

(22) PCT Filed: Jun. 13, 2007

(86) PCT No.: PCT/IL2007/000716
§ 371 (c)(1),
(2), (4) Date: Sep. 10, 2009

(87) PCT Pub. No.: WO2007/144883
PCT Pub. Date: Dec. 21, 2007

(65) Prior Publication Data
US 2010/0168648 A1    Jul. 1, 2010

Related U.S. Application Data

(60) Provisional application No. 60/812,951, filed on Jun. 13, 2006.

(51) Int. Cl.
*A61M 31/00* (2006.01)

(52) U.S. Cl. .................................. 604/515; 604/514
(58) Field of Classification Search .............. 604/22, 604/514, 515
See application file for complete search history.

(56) References Cited

U.S. PATENT DOCUMENTS

| 4,078,052 A | 3/1978 | Papahadjopoulos |
| 4,780,212 A | 10/1988 | Kost et al. |
| 5,163,421 A | 11/1992 | Bernstein et al. |
| 5,458,140 A | 10/1995 | Eppstein et al. |
| 7,037,277 B1 | 5/2006 | Smith et al. |

FOREIGN PATENT DOCUMENTS

| WO | 98/48711 A1 | 11/1998 |
| WO | 01/70330 A2 | 9/2001 |
| WO | 02/058530 A2 | 8/2002 |
| WO | 2007/066335 A2 | 6/2007 |

OTHER PUBLICATIONS

Sundaram, et al., "An Experimental and Theoretical Analysis of Ultrasound-Induced Permeabilization of Cell Membranes," Biophys. J. (2003), vol. 84, No. 5, pp. 3087-3101.

*Primary Examiner* — Bhisma Mehta
(74) *Attorney, Agent, or Firm* — Vorys, Sater, Seymour and Pease LLP; Susanne M. Hopkins

(57) ABSTRACT

The invention provides a system and method for trans-fetal membranes transport. A source of ultrasound sonication is used to deliver ultrasound sonication to fetal membranes to enhance the permeability of the fetal membranes of a gestational sac. In one embodiment, a device is used to collect substances transported from the interior of the gestational sac to the exterior of the gestational sac, such as amniotic or coelomic fluid. In another embodiment a device is used to deliver one or more substances, such as a drug, to an external surface of the fetal membranes.

9 Claims, 9 Drawing Sheets

SYSTEM AND METHOD FOR TRANSFETAL (AMNION-CHORION) MEMBRANES TRANSPORT

FIELD OF THE INVENTION

This invention relates to medical devices, and more particularly to such devices for procedures and devices making use of ultrasound (US).

LIST OF PRIOR ART

The following is a list of prior art, which is considered to be pertinent for describing the state of the art in the field of the invention.
  1. U.S. Pat. No. 4,078,052 to Papahadjopoulos;
  2. International Patent Application No. PCT IL2006/001404 to Barenholz et al;
  3. U.S. Pat. No. 4,780,212 to Kost;
  4. Sundaram, J., Mellein B. R., and Mitragotri S., An experimental and theoretical analysis of ultrasound-induced permeabilization of cell membranes. Biophysical J. 2003 84, 3087-3101.
  5. U.S. Pat. No. 5,458,140 to Eppstein, et al.
  6. U.S. Pat. No. 7,037,277 to Smith et al.
  7. U.S. Pat. No. 5,163,421 to Bernstein et al.
  8. International Patent Application Publication No. WO01/70330 to Custer et al.

BACKGROUND OF THE INVENTION

Prenatal testing involves testing a fetus for the presence of various hereditary or spontaneous genetic disorders, such as Down syndrome. One of the most common procedures for detecting abnormalities before birth is amniocentesis in which a sample of the fluid surrounding the fetus (amniotic fluid) is obtained. In amniocentesis, after anesthetizing an area of abdominal skin, a needle is inserted through the abdominal wall into the amniotic cavity. During the procedure, ultrasonography is performed so that the position of the fetus can be monitored and the needle guided into place without touching the fetus. Amniotic fluid is collected through the needle into a syringe, and the needle is then removed. Another fetal examination includes chorionic villus sampling (CVS). Both amniocentesis and CVS are invasive, and as such carry a small but definite risk to the mother and fetus. After amniocentesis, the chance of miscarriage due to the procedure is about 1 in 200.

Ultrasound has been used in a number of medical applications. Examples of clinical applications of ultrasound include imaging, stimulation of the healing of soft tissue, during topical application of a medication, and for enhancement of transdermal drug delivery into the circulatory system. In addition, ultrasound has also been used for selectively altering the permeability of cell membranes. This alteration is reversible and the effect can be controlled as to its extent and rate.

Further, a method for non-invasively monitoring the concentration of an analyte in an individual's body using ultrasound and for increasing permeability of a selected area of the individual's body surface have been described. The method makes use of chemical enhancers in combination with ultrasound sonication.

SUMMARY OF THE INVENTION

The present invention provides a system and method for enhancing the permeability of fetal membranes (amnion and chorion). The enhanced permeability may be utilized to withdraw substances from the gestational sac through the fetal membranes, or to introduce substances into the gestational sac through the fetal membranes, without inserting a needle through the fetal membranes into the interior of the gestational sac.

The invention is based on the finding that the permeability of fetal membranes is increased by exposure to ultrasound sonication. Without being bound to a particular theory, it is believed that exposure of the fetal membranes to ultrasound sonication causes cavitation in the membranes and/or substances in contact with the fetal membranes, leading to micropore formation and enhanced permeability. It is further believed that the micro-pores eventually reseal after the ultrasound sonication is terminated.

In one embodiment of the invention, a probe containing an ultrasound source is inserted through the vagina and positioned with the ultrasound source in either the vagina or cervix. Ultrasound sonication is directed to a portion of the fetal membranes adjacent to the cervix, in order to enhance the permeability of the fetal membranes. In an application of the invention where a sample of a substance in the gestational sac, such as amniotic fluid or coelomic fluid, is to be obtained, the substance may be collected under suction into a receptacle. In an application where a substance is to be delivered into the gestational sac, the substance is delivered to the exterior surface of the permeabilized fetal membranes and allowed to diffuse into the interior of the gestational sac.

The ultrasound sonication may be performed using a continuous or pulsed sonication mode. The fetal membranes may be sonicated by a single ultrasound source or by two or more ultrasound sources sonicating the fetal membranes from different directions while being focused on the same region of the fetal membranes.

The ultrasound sonication will typically have intensity in a range between about 1 to 10 Watt/cm$^2$.

Thus, in one of its aspects, the present invention provides a system for trans-fetal membrane transport comprising:
  (a) a source of ultrasound sonication configured to deliver ultrasound sonication to fetal membranes to enhance the permeability of the fetal membranes of a gestational sac; and
  (b) a device selected from:
    a device adapted to collect substances transported from an interior of the gestational sac to an exterior of the gestational sac; and
    a device to deliver one or more substances to an external surface of the fetal membranes.

In another of its aspects, the invention provides a method for trans-fetal membrane transport comprising:
  (c) delivering ultrasound sonication to the fetal membranes of a gestational sac to increase a permeability of the fetal membranes; and
  (d) collecting substances transported from an interior of the gestational sac to an exterior of the gestational sac or delivering one or more substances to an external surface of the fetal membranes.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EXEMPLARY EMBODIMENTS

Figure 1:
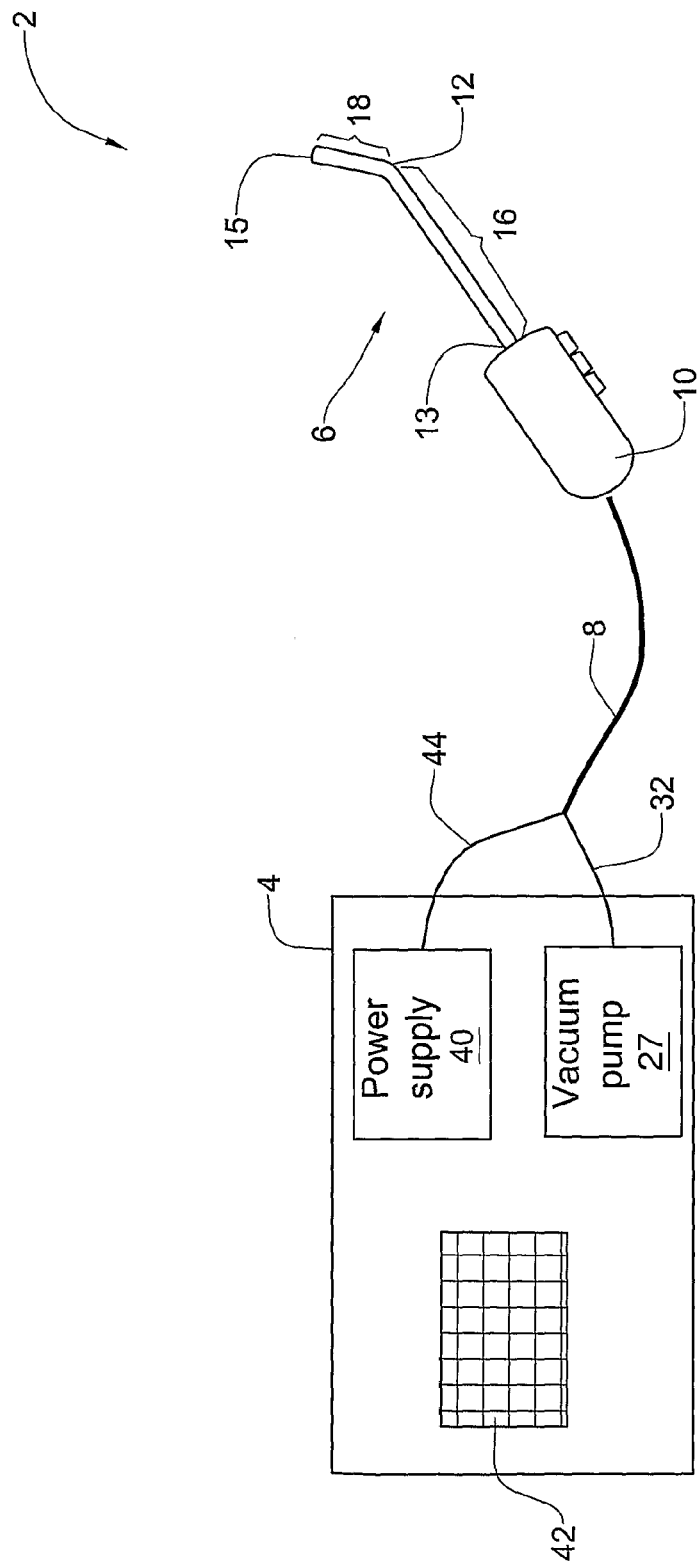
FIG. 1 shows a system for trans-fetal membrane transport according to one embodiment of the invention.

FIG. 1 shows a system generally indicated by 2 for transfetal membrane transport, in accordance with one embodiment of the invention. The system 2 may be used to generate transport through the fetal membranes from the interior of the gestational sac to the exterior, for example, to obtain a sample of amniotic fluid or coelomic fluid.

The system 2 comprises a control unit 4 and a probe unit 6 which is attached to the control unit 4 via a harness 8. The probe unit 6 has a handle 10, a shaft 12, a proximal end 13 and a distal end 15. The shaft 12 may be rigid and permanently bent or curved to form a vaginal portion 16 and a cervical portion 18. Alternatively, the shaft may be flexible so as to be bendable into an angled shape having a vaginal portion and a cervical portion.

Figure 2:
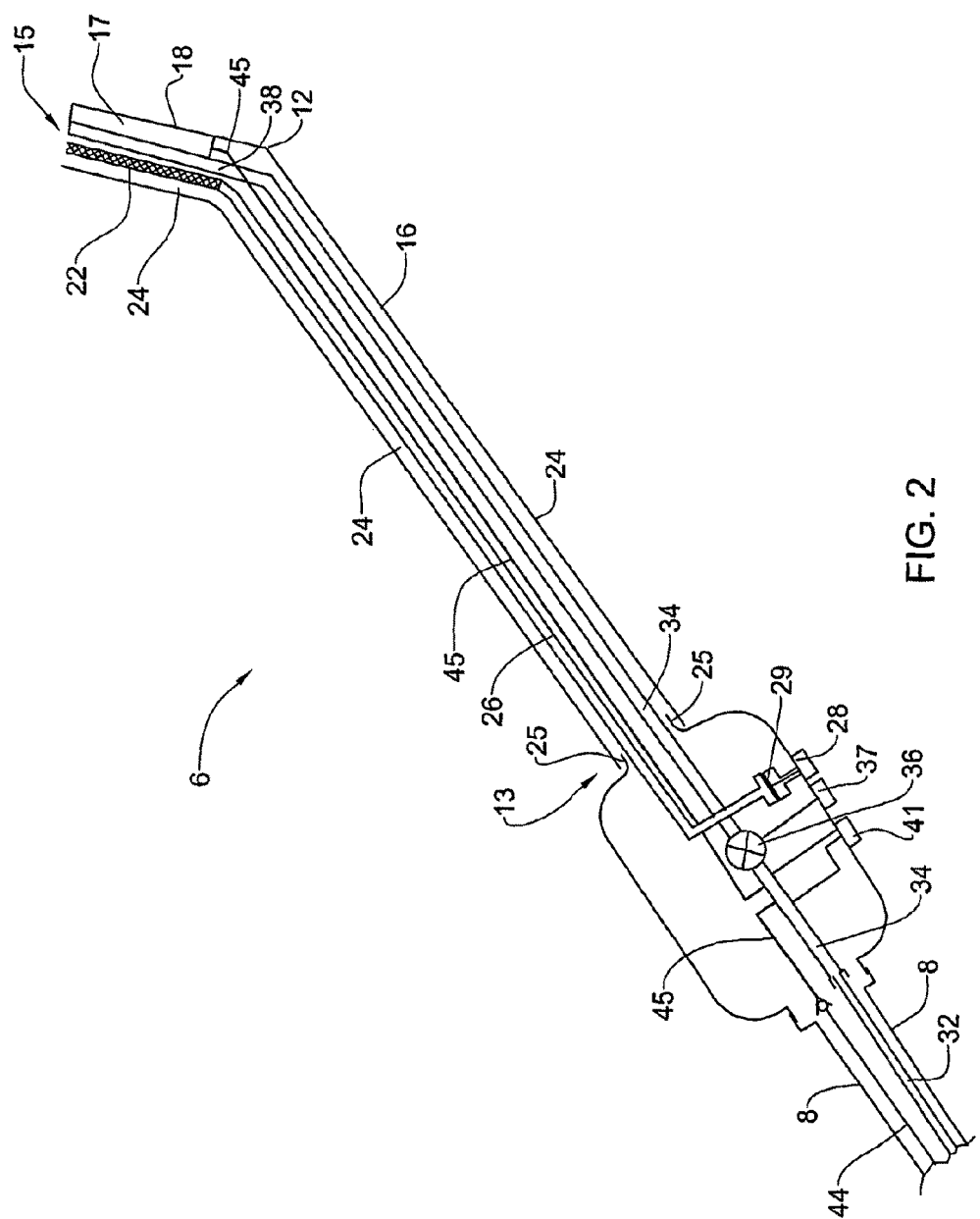
FIG. 2 shows a probe unit for use in the embodiment of FIG. 1.

FIG. 2 shows the probe unit 6 in greater detail. The cervical portion 18 comprises an ultrasound source 17 that emits ultrasound waves from the distal end 15 of the probe unit 6. The ultrasound source 17 is contained in an outer sleeve 24 that extends along the length of the shaft 12. The outer sleeve 24 is made from a biocompatible material such as Teflon or silicone. The outer sleeve 24 is attached to the handle 10 at a collar 25. The outer sleeve is preferably detachable from the handle 10, and is most preferably disposable. The probe unit 6 is also provided with a coupling medium delivery system which delivers an acoustic coupling medium to the distal end of the probe unit 6 for acoustic coupling of the ultrasound sonication to the body tissues, as explained below. A reservoir 22 is used to store an amount of an ultrasound coupling medium. Depressing a spring-biased push button 28 drives a piston 29 to create an elevated pressure in the reservoir 22 via a conduit 26 that urges the coupling medium to flow from the reservoir 22 out of the distal end 15 of the probe unit 6.

The system 2 is also provided with a vacuum system that draws into the probe unit 6 substances released from the interior of the gestational sac to the exterior as a result of the ultrasound sonication of the gestational sac, as explained below. A vacuum pump 27 may be located in the control unit 4, as shown in FIG. 1, or may be external to the control unit 4. The vacuum pump 27 creates a negative pressure in a receptacle 38 in the sleeve 24 via a vacuum hose 32 in the harness 8, and a connecting channel 34 in the handle 10. A normally closed valve 36 in the connecting channel 34 is opened by depressing a spring biased push-button switch 37 when it is desired to create a negative pressure in the receptacle 38, as explained below.

In an alternative embodiment (not shown) drawing of substances released from the gestational sac into the probe unit 6 utilizes a solution of high osmotic pressure that is applied to the external surface of the gestational sac. The high osmotic pressure solution draws amniotic and/or ceolomic fluid and dissolved or suspended substances across the fetal membranes by osmosis from the interior to the exterior of the gestational sac where the substances are collected in a receptacle.

The control unit contains a power supply 40 that is connected to the ultrasound transducer 17 via wires 44 in the harness 8 that connect with wires 45 in the probe unit 6. Closing a switch 41 on the handle 10 activates the ultrasound source 17 to the power supply 40. The control unit also contains a user input device, such as a key pad 42 that allows a user to input values of various parameters relating to the ultrasound sonication, such as intensity, pulse duration, pulse repetition rate or wavelength, as well as details of the individual being examined.

Figure 3B:
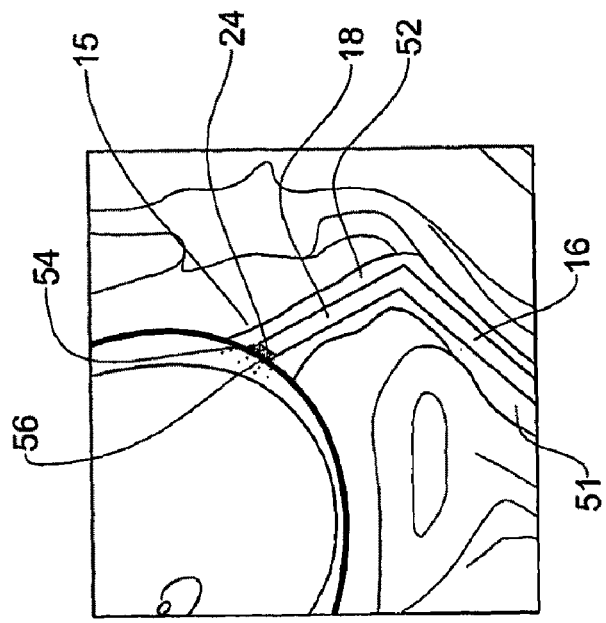
FIGS. 3a and 3b show the probe of FIG. 2 inserted in a vagina and a cervix.
Figure 3A:
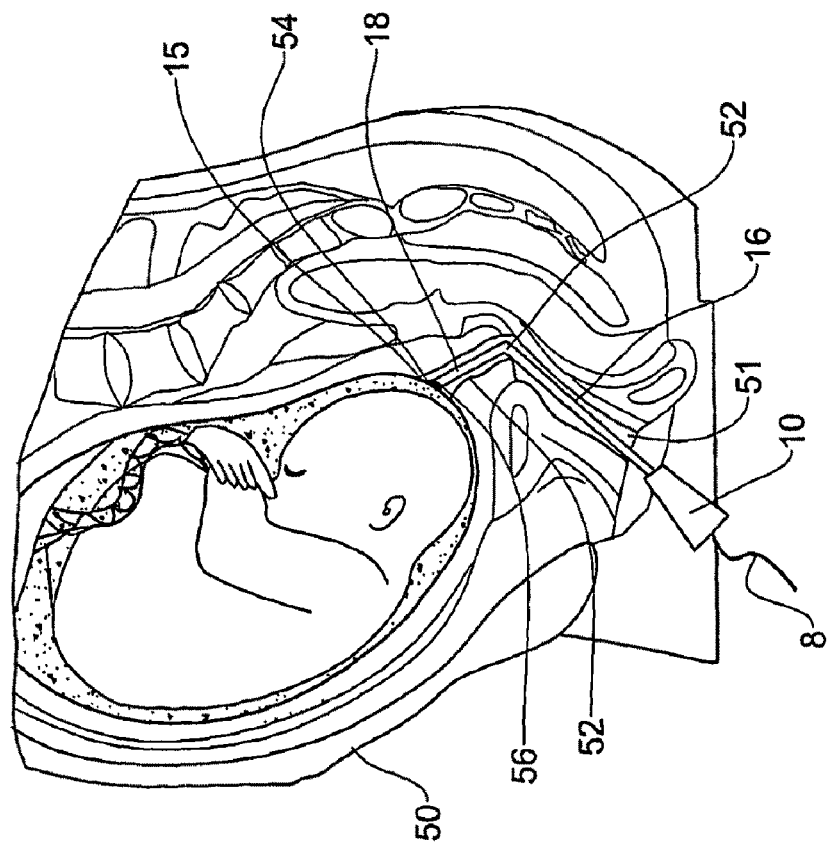

FIGS. 3a and 3b show use of the system 2 to collect a body substance such as an amniotic fluid sample or a coelomic fluid sample from an individual 50. The shaft 12 of the probe unit 6 is introduced into the vagina 51 and positioned with the vaginal portion 16 in the vagina 51 and the cervical portion 18 in the cervix 52. Positioning of the probe unit 6 in the body may be monitored by external ultrasonography to ensure proper placement of the probe unit 6 in the body. A small amount of coupling medium is then expelled from the distal end 15 of the probe unit 6 by depressing the push-button 28. The distal end 15 of the probe is then apposed to a portion of the fetal membranes 56 adjacent to the cervix 52 in order to ensure acoustic coupling of ultrasound sonication to the portion 56 of the fetal membranes. The ultrasound activation button 41 is then depressed to activate the ultrasound transducer 17. Substances withdrawn from the gestational sac may be collected during and/or after the ultrasound sonication by depressing the push-button 28 to open the vacuum valve 36. Ultrasound sonication 54 emitted from the ultrasound source 17 is directed to the portion of the fetal membranes 56 adjacent to the cervix 52. As demonstrated below, exposure of the fetal membranes 56 to the ultrasound sonication 54 increases the permeability of the fetal membranes. The permeability of the fetal membranes 56 may be monitored during and after the sonication by measuring the conductivity of the membranes (not shown). Substances passing out of the gestational sac as a result of the increased permeability, such as amniotic or coelomic fluid, are drawn into the distal end 15 of the probe unit 6 under the influence of the vacuum system and/or osmotic pressure when present, and are collected in the receptacle 38. After collection of substances passing through the fetal membranes, the vacuum is turned off, and the probe unit 6 is removed from the body. Substances collected in the receptacle 38 are then removed from the receptacle 38 and are analyzed.

Figure 4:
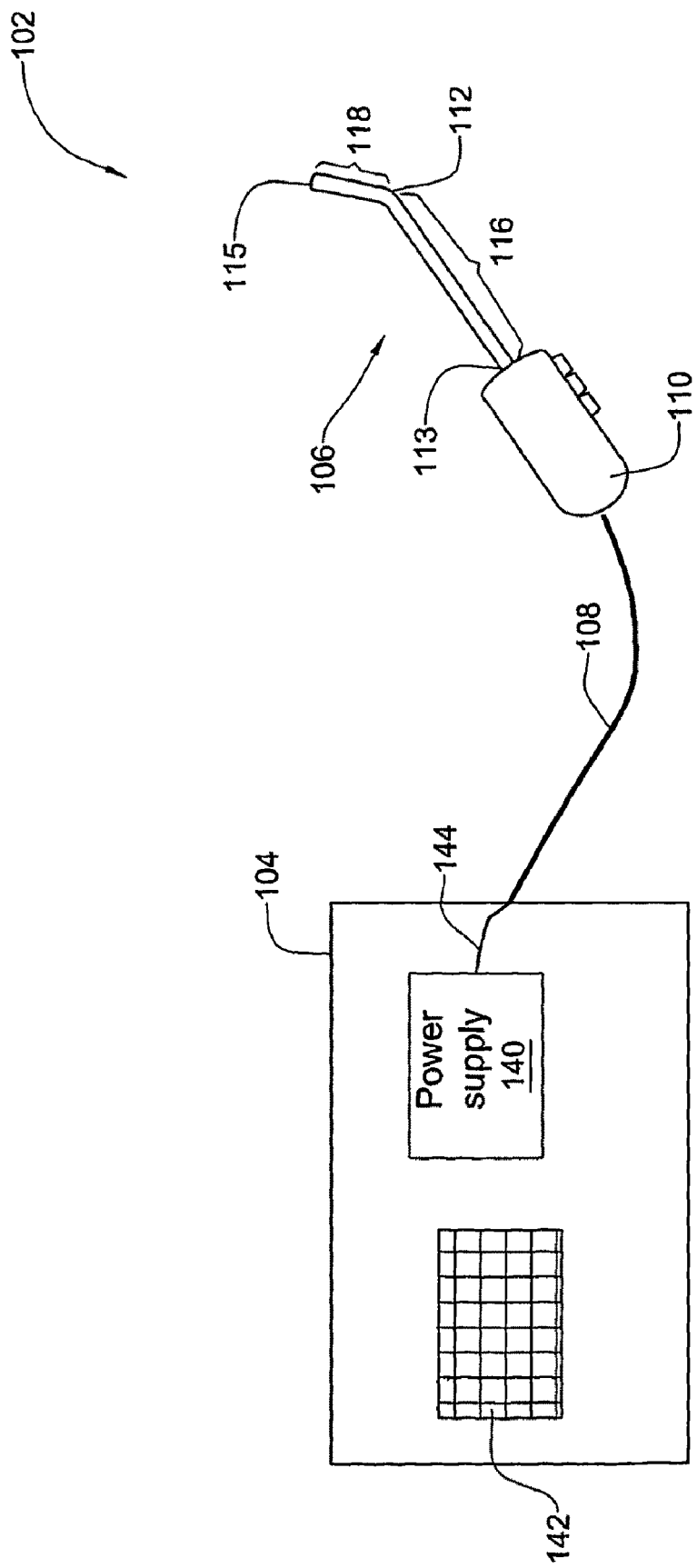
FIG. 4 shows a system for trans-fetal membrane transport according to another embodiment of the invention.

FIG. 4 shows a system generally indicated by 102 for transfetal membranes transport, in accordance with another embodiment of the invention. The system 102 may be used to transport substances such as drugs from the exterior of the fetal membranes into the gestational sac.

The system 102 comprises a control unit 104 and a probe unit 106 which is attached to the control unit 104 via a harness 108. The probe unit 106 has a handle 110, a shaft 112, a proximal end 113 and a distal end 115. The shaft 112 may be rigid and permanently bent, or may be bendable to form a vaginal portion 116 and a cervical portion 118.

Figure 5:
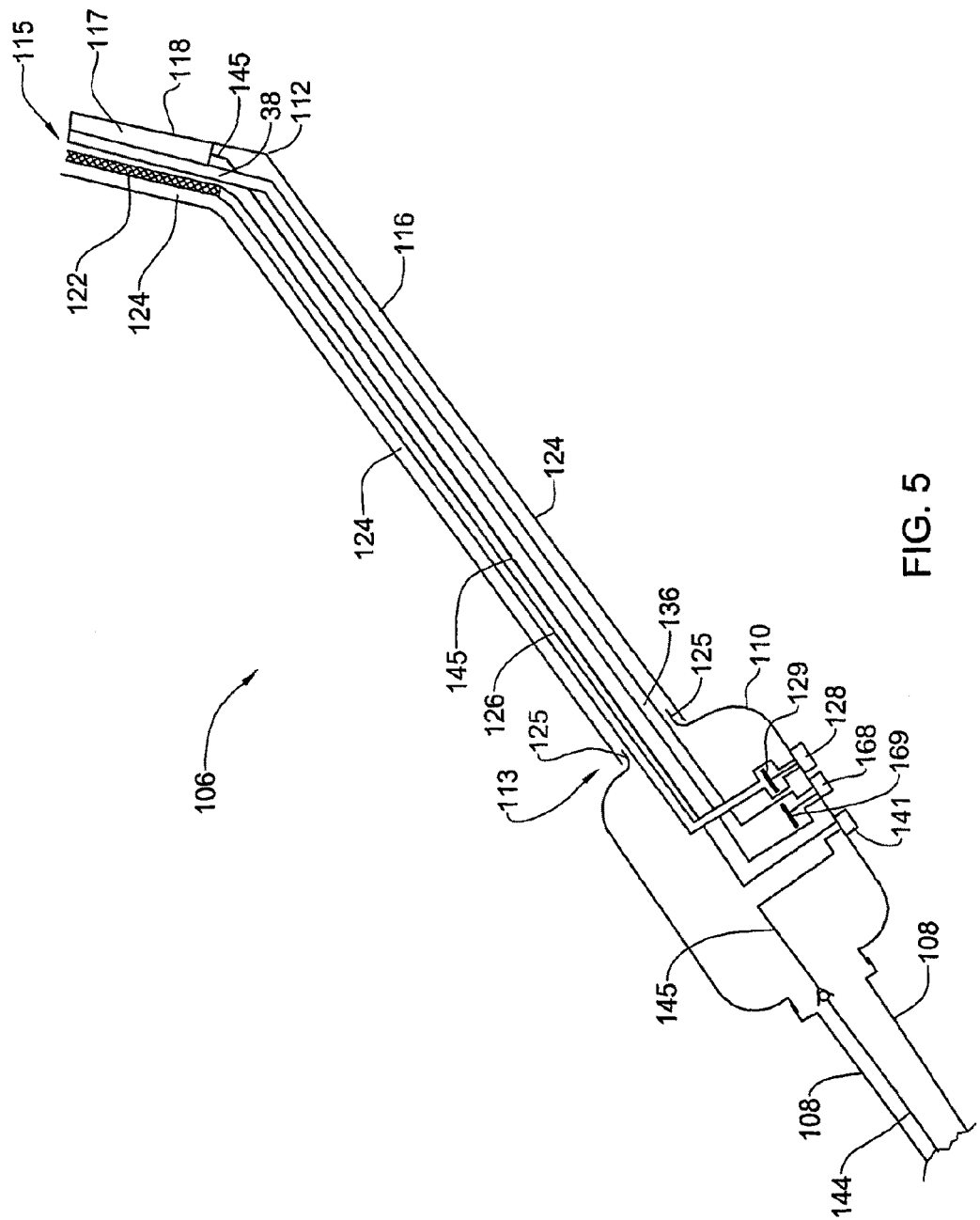
FIG. 5 shows a probe unit for use in the embodiment of FIG. 1.

FIG. 5 shows the probe unit 106 in greater detail. The cervical portion 118 comprises an ultrasound source 117 that emits ultrasound waves from a distal end 115 of the probe unit 106. The ultrasound source 117 is contained in an outer sleeve 124 that extends along the length of the shaft 112. The outer sleeve 124 is attached to the handle 110 at a collar 125. The outer sleeve is preferably detachable from the handle 110, and is most preferably disposable. The probe unit 106 is also provided with a coupling medium delivery system which delivers an acoustic coupling medium to the distal end of the probe unit 106 for acoustic coupling of the ultrasound sonication to the body tissues, as explained below. A reservoir 122 is used to store an amount of an ultrasound coupling medium. Depressing a spring-biased push button 128 drives a piston 129 to create an elevated pressure in the reservoir 122 via a conduit 126 that urges the coupling medium to flow out from the reservoir 122 to the distal end 115 of the probe unit 106.

The system 102 is provided with a delivery system for delivering one or more substances, such as drugs, to the external surface of the gestational sac. The one or more substances are stored in a reservoir. Depressing a spring-biased push button 168 drives a piston 169 to create an elevated pressure in the reservoir via a conduit that urges the substances to flow from the reservoir out of the distal end 115 of the probe unit 106.

The control unit contains a power supply 140 that is connected to the ultrasound transducer 117 via wires 144 in the harness 108 that connect with wires 145 in the probe unit 106. Closing a switch 141 on the handle 110 activates the ultrasound source 117. The control unit also contains a user input device, such as a key pad 142 that allows a user to input values of various parameters relating to the ultrasound sonication, such as intensity, pulse duration, pulse repetition rate or wavelength, as well as details of the individual being examined.

Figure 6B:
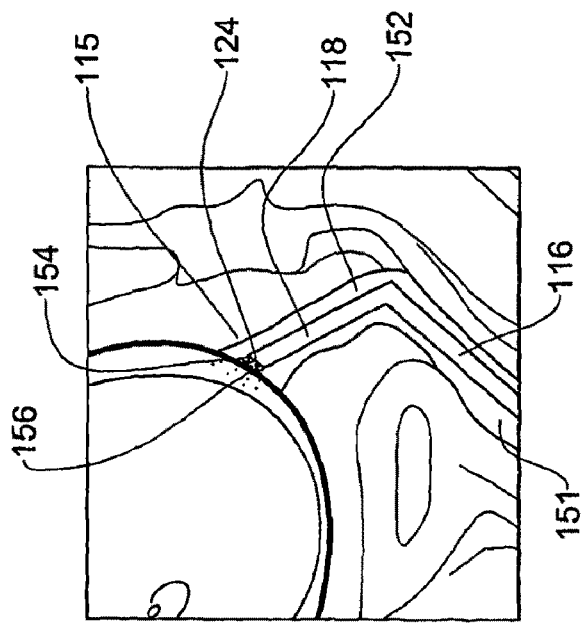
FIGS. 6a and 6b show the probe of FIG. 2 inserted in a vagina and a cervix.
Figure 6A:
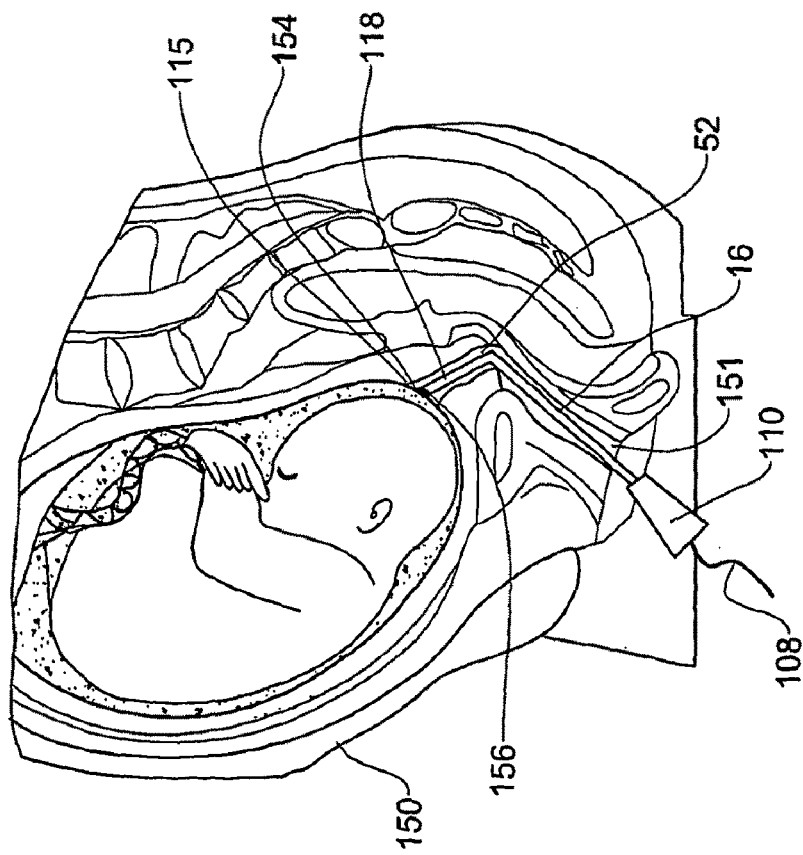

FIGS. 6a and 6b show use of the system 102 to deliver the one or more substances, such as a drug, into a gestational sac of an individual 150. The shaft 112 of the probe unit 106 is introduced into the vagina 151 and is positioned with the vaginal portion 116 in the vagina 151 and the cervical portion 118 in the cervix 152. A small amount of coupling medium is then delivered to the distal end 115 of the probe unit 106 by depressing the push-button 128. The distal end 115 of the probe is then apposed to a portion of the fetal membranes 156 adjacent to the cervix 152 in order to ensure acoustic coupling of ultrasound sonication to the portion 156 of the fetal membranes. The ultrasound activation switch 141 is then depressed to activate the ultrasound source 117. The one or more substances are delivered to the distal end 115 of the shaft 112 by depressing the push-button 168, during or after the ultrasound sonication. Ultrasound sonication 154 emitted from the ultrasound source 117 is directed to the portion of the fetal membranes 156 adjacent to the cervix 52. As demonstrated below, exposure of the fetal membranes 156 to the ultrasound sonication 154 increases the permeability of the fetal membranes. The permeability of the membranes 156 may be monitored during and after the sonication by measuring the electrical conductivity of the membranes (not shown). The substances delivered to the distal end 115 of the shaft 112 are available to diffuse across the fetal membranes as a result of the increased permeability. After delivery of the substances, the probe unit 106 is removed from the body.

In one embodiment, the ultrasound sonication has a frequency of between about 2 Q kHz to about 3 MHz. In a preferred embodiment the ultrasound sonication has a frequency between about 20 kHz and about 500 kHz, and more preferably between about 20 kHz and 100 kHz. This range is referred to at times by the term "low frequency ultrasound sonication" (LFUS). In one embodiment, continuous ultrasound sonication for about 5 sec to about 30 min, more preferably, from about 30 sec to about 10 min, is used.

EXPERIMENTAL RESULTS

Example 1

In Vitro Permeability of Amniotic Membrane

Figure 7A:
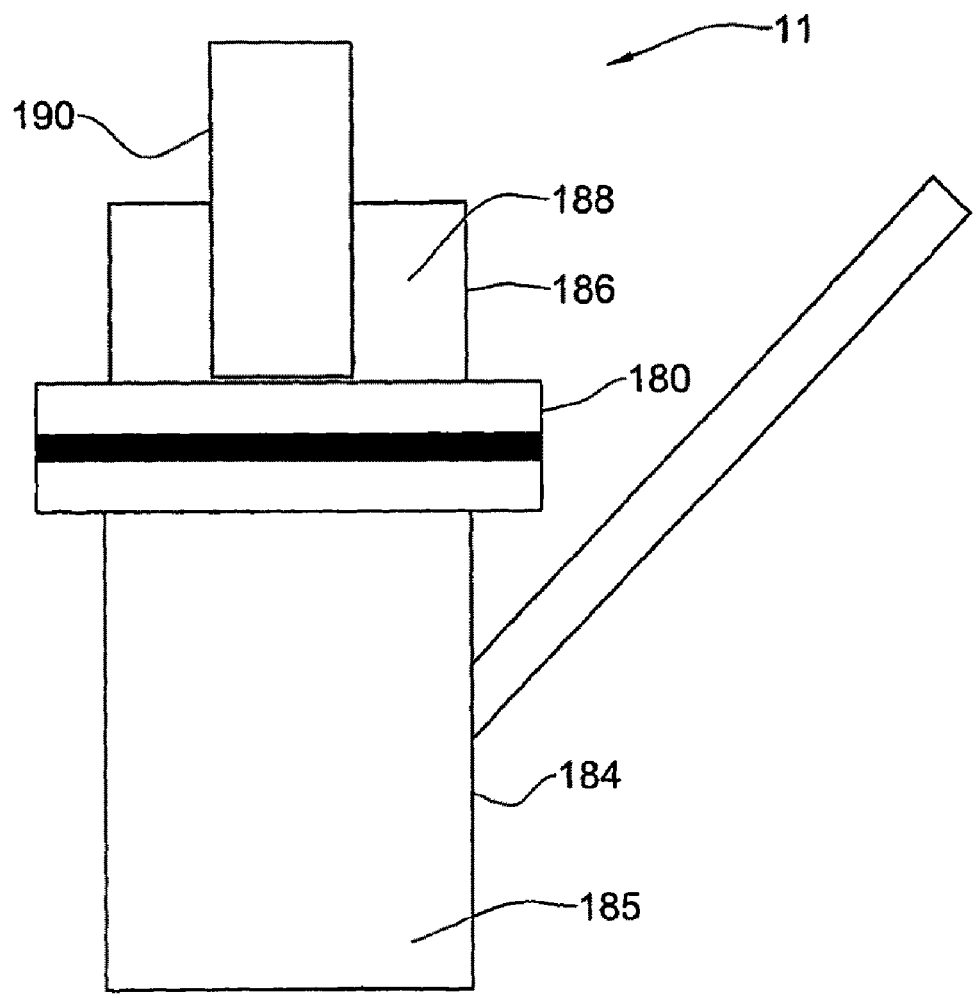
FIGS. 7a and 7b show a system for in vitro trans-fetal membrane transport.

The permeability of postpartum human fetal membranes (obtained from Hillel Yaffe Medical Center, Israel) upon exposure to ultrasound was determined. As shown in FIG. 7a, fetal membranes 180 (a piece of a gestational sac) were mounted on a glass vertical diffusion cell 11 with the maternal side facing a donor compartment 186. A receiver compartment 184 was filled with phosphate Buffer Saline (PBS) 185. The donor compartment 186 was filled with an ultrasound coupling medium 188 comprising 1% Sodium Dodecyl Sulphate (SDS) in phosphate Buffer Saline (PBS). The tip of a 1 cm (diameter) ultrasound transducer (VCX-400 (Sonics & Materials, Newtown, Conn.) 190 was immersed in the coupling medium 188 at a distance of 1 mm from the membranes 180. The membranes were then sonicated with ultrasound sonication at a frequency of 20 KHz for a duration of 10 minutes, and at various intensities as indicated below and with a duty cycle of 50% (0.5 sec on, 0.5 sec off). In control experiments, the ultrasound sonication was omitted.

Figure 7B:
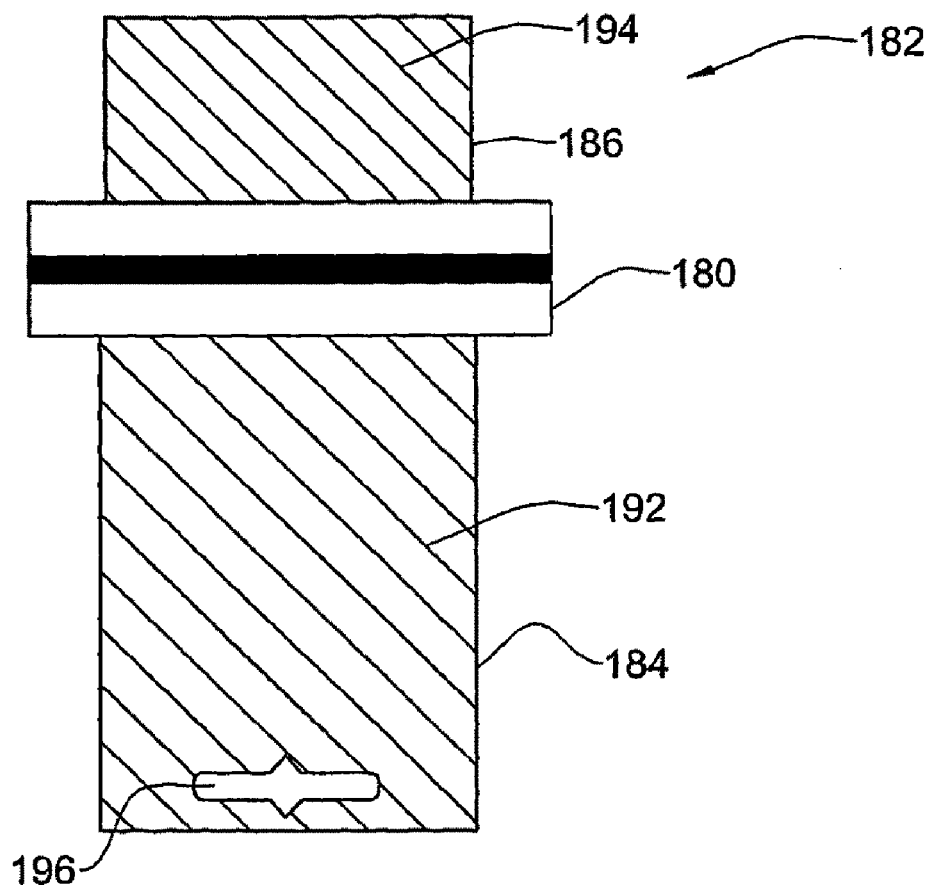

After 10 minutes of the pulsed sonication, the coupling medium 188 was removed from the donor compartment 186, the membranes 180 were removed and washed with PBS, and the PBS 185 was removed from the receiver compartment 184. Then, as shown in FIG. 7b, the sonicated membranes 180 were remounted on the diffusion cell 182, this time with the maternal surface facing the receiver compartment 184, and fresh PBS 192 was added to the receiver compartment 184 together with a magnetic stirring bar 196. 2 ml of Dextran (average molecular weight 40 KDa) conjugated to the fluorescent label FITC (Fluorescein Isothiocyanate-Dextran)) 194 at a concentration of 12.5 p.M in PBS was added to the donor compartment 186. From this point, the diffusion cell 182 was protected from light, in order to prevent fluorescent bleaching of the fluorescent label. 1 ml samples were withdrawn from the receiver compartment 184, at different times and analyzed for the concentration of the fluorescent label.

Figure 8:
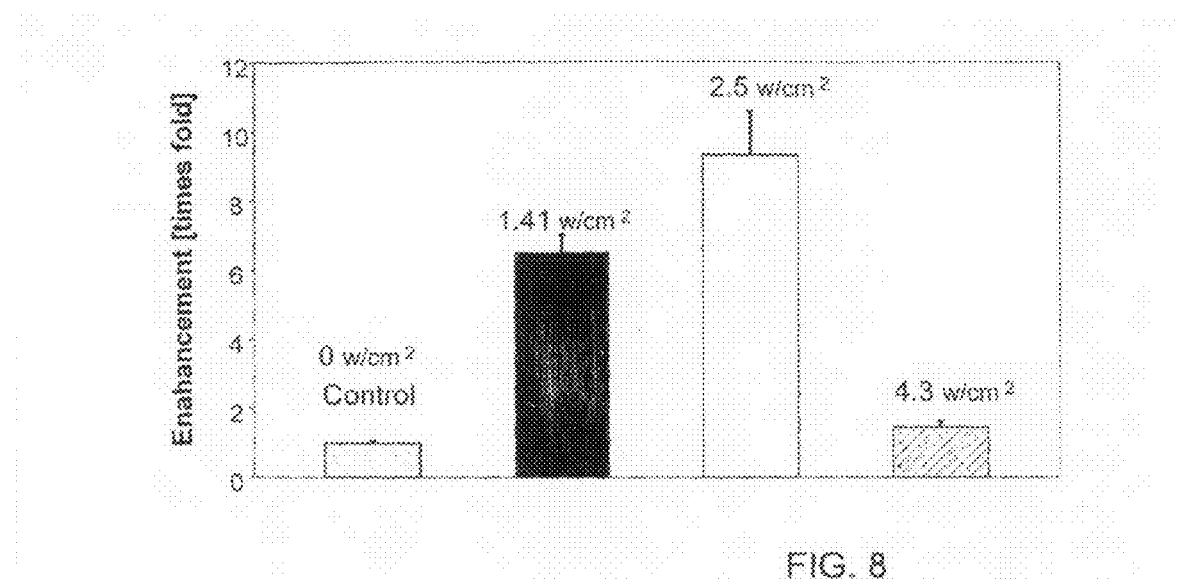
FIG. 8 shows the effect of ultrasound sonication at the indicated intensities of postpartum human fetal membranes on membrane permeability.

From the rate of increase in the concentration of the fluorescence in the receiver compartment 184, the extent of permeability enhancement of the membrane, in comparison to a control membrane not sonicated with ultrasound sonication was calculated. FIG. 8 shows the enhancement in permeability of the membrane, compared to the non-sonicated control, for the different ultrasound intensities used. An optimal effect was observed at an intensity of about 2.5 Watts/cm$^2$ (at a duty cycle of 50%). The decline in permeability at higher intensities may due to a gas decoupling effect on the surface of the ultrasound probe.

Figure 9:
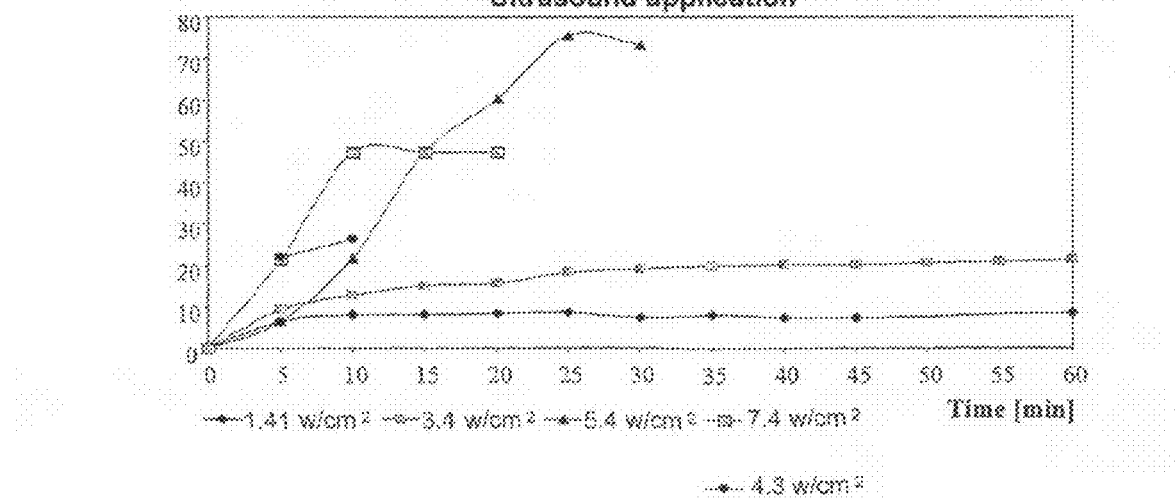
FIG. 9 shows the effect of ultrasound sonication at various intensities and a 50% duty cycle of postpartum human fetal membranes on the electrical conductivity of the membrane

During the ultrasound sonication, the electrical conductivity of the postpartum membranes 180 was determined at five minute intervals. FIG. 9 shows the enhancement in conductivity of the membranes as a function of time during ultrasound sonication at the intensities indicated. At intensity of 4.3 Watts/cm$^2$ (at a duty cycle of 50%) and above, the membrane ruptured after 10 to 30 minutes of irradiation.

The invention claimed is:

1. A method for trans-fetal membrane transport comprising:
   (a) delivering ultrasound sonication to fetal membranes of a gestational sac to increase a permeability of the fetal membranes; and
   (b) collecting one or more substances transported from an interior of the gestational sac to an exterior of the gestational sac.

2. The method of claim 1, wherein the ultrasound sonication is delivered using an ultrasound source inserted into a vagina.

3. The method of claim 1, wherein the ultrasound sonication is delivered using an ultrasound source inserted into a cervix.

4. The method of claim 1, comprising delivering an acoustic coupling material between the ultrasound source and a body tissue.

5. The method of claim 1, wherein the one or more substances are collected in a receptacle positioned in a vagina or a cervix.

6. The method of claim 1, comprising drawing the one or more substances away from the fetal membranes by a vacuum.

7. The method of claim 1, comprising drawing the one or more substances away from the fetal membranes by a high osmotic solution.

8. The method of claim 1, wherein the one or more substances is an amniotic fluid or a coelomic fluid.

9. The method of claim 1, comprising monitoring electrical conductivity of the fetal membranes.

* * * * *